Figure 1:
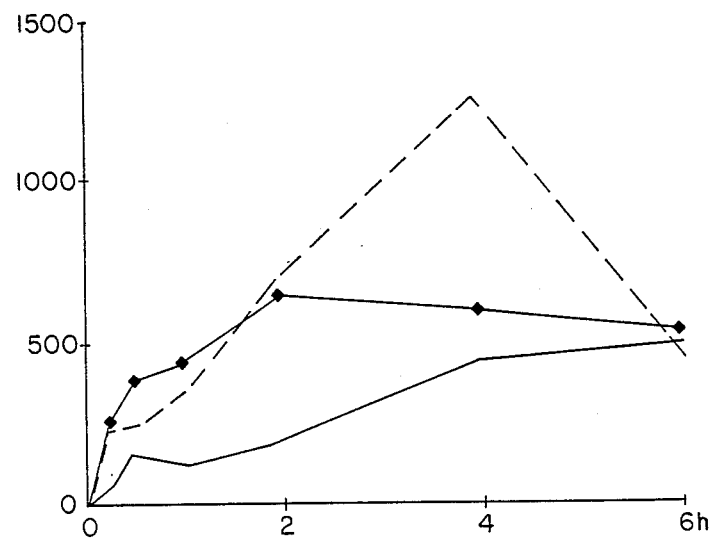

United States Patent [19]

Löhner et al.

[11] Patent Number: 4,849,418
[45] Date of Patent: Jul. 18, 1989

[54] TRANSDERMALLY ABSORBABLE WATER-CONTAINING PREPARATIONS OF ARYLPROPIONIC ACID DERIVATIVES AND PROCESS FOR PREPARING SAME

[75] Inventors: Manfred Löhner, Bonn; Hans H. Wagener, Meckenheim, both of Fed. Rep. of Germany

[73] Assignee: Dolorgiet Beteiligungs-GmbH, Fed. Rep. of Germany

[21] Appl. No.: 101,532

[22] Filed: Nov. 16, 1987

Related U.S. Application Data

[63] Continuation-in-part of Ser. No. 887,958, Jul. 22, 1986, abandoned.

[30] Foreign Application Priority Data

Sep. 12, 1985 [DE] Fed. Rep. of Germany ....... 3532562

[51] Int. Cl.$^4$ ................... A61K 31/19; A61K 31/61
[52] U.S. Cl. ................... 514/163; 514/356; 514/570; 514/944; 514/947
[58] Field of Search ................... 514/570, 163

[56] References Cited

U.S. PATENT DOCUMENTS

| | | |
|---|---|---|
| 3,740,421 | 6/1973 | Scholka . |
| 4,511,563 | 4/1985 | Schmolka ........................... 514/162 |
| 4,533,546 | 8/1985 | Fishi et al. ........................... 424/81 |
| 4,534,980 | 8/1985 | Itoh et al. ........................... 514/570 |
| 4,555,524 | 11/1985 | Gruber et al. ........................... 514/570 |

FOREIGN PATENT DOCUMENTS

| | | |
|---|---|---|
| 0072462 | 2/1983 | European Pat. Off. . |
| 0178436 | 4/1986 | European Pat. Off. . |
| 1617480 | 4/1972 | Fed. Rep. of Germany . |
| 2708152 | 9/1977 | Fed. Rep. of Germany . |

OTHER PUBLICATIONS

"Rote Liste 1985", Herausgeber: Bundesverband der Pharmazeutischen Industrie e. V., 6000 Frankfurt Germany, 9/9/1985.
Chemical Abstracts, vol. 104, p. 392, May 13, 1986.
Chemical Abstracts, vol. 10, No. 178, (C-355)[2234] 6/21/1986, European Search Report.

*Primary Examiner*—Leonard Schenkman
*Attorney, Agent, or Firm*—Wegner & Bretschneider

[57] ABSTRACT

Transdermally absorbable water-containing preparations of therapeutically active arylpropionic acid derivatives comprises 1 to 15% by weight of such active ingredient, from 10 to 40% by weight of polyoxyethylene polyoxypropylene copolymers, from 10 to 50% by weight of one or more physiologically acceptable organic solvents, optionally up to 1% by weight of preservatives, colorants and/or perfumes, and at least 10% by weight of water. From polyoxyethylene polyoxypropylene copolymers having a relative molecular weight of more than 6,000 there may also be prepared gels, if certain ratios of amounts are chosen.

16 Claims, 1 Drawing Sheet

TRANSDERMALLY ABSORBABLE WATER-CONTAINING PREPARATIONS OF ARYLPROPIONIC ACID DERIVATIVES AND PROCESS FOR PREPARING SAME

This is a continuation-in-part of application Ser. No. 887,958, filed July 22, 1986, now abandoned.

The present invention relates to transdermally absorbable water-containing preparations of therapeutically active arylpropionic acid derivatives and to a process for making said preparations which are in the form of liniments, however preferably in the form of gels.

Arylpropionic acid derivatives such as, e.g., flurbiprofen=2-(2-fluorobiphenyl-4-yl)-propionic acid, ibuprofen=2-(4-isobutylphenyl)-propionic acid, ketoprofen=2-(3-benzoylphenyl)propionic acid or naproxen=(+)-2-(6-methoxy-2-naphthyl)propionic acid are known from Martindale, The Extra Pharmacopoeia, 28. edition, 1982, pages 255, 256, 261 and 264 as medicaments having antiinflammatory and analgesic properties. They are used for the treatment of rheumatoid arthritis or other inflammatory articular diseases, soft tissue rheumatism and gout.

The arylpropionic acid derivatives are most frequently administered in the form of tablets and dragees. However, the oral administration also causes disadvantageous effects such as gastrointestinal troubles, vertigo, nausea and headache. For patients suffering from gastric or duodenal ulcer, oral treatment with these medicaments is contraindicated.

An active ingredient which is transdermally absorbed reaches the target organ directly with evasion of the first-pass-metabolism, i.e. the first metabilization in the liver, which route is inevitable upon oral administration.

Thus it becomes possible to reduce the dose of the active ingredient required for producing the pharmacodynamic effect and also to avoid the drawbacks inherent in oral application.

For this reason attempts have already been made to prepare medicaments containing arylpropionic acid derivatives for transdermal application. From the German Patent Specification No. 32 05 504 or the European Unexamined Patent Application EPO 087 062 there is known a composition in the form of a cream containing ibuprofen.

From Boll. Chim. Farm. 119 (1980), page 738, dermatological formulations comprising various active substances are known which were investigated with respect to the in vitro release (diffusion rate). It appears therefrom that water-containing preparations show higher release rates than water-free preparations. The experiments were uniformly carried out using 2.5% by weight of the active ingredient. Higher concentrations were not investigated. There are no indications that would allow a conclusion that the products thus obtained have sufficient therapeutic activities.

In the European Published Application EP-OS 0 127 840 there have been described compositions comprising some arylacetic acid and arylpropionic acid derivatives which in their formulation correspond to the gel of the aforementioned publication. Only compositions containing the arylacetic acid derivative Ibufenac in different concentrations were examined for their activities.

From the German Published Application DE-OS 31 19 017 there are known gels comprising the arylpropionic acid derivatives ketoprofen and flurbiprofen which, in a preparation containing 1%, were investigated for percutaneous absorption by humans and for antiinflammatory activity in rats. These gels contain further auxiliary materials in addition to the carboxyvinyl polymer familiar as a gel base.

DE-OS 33 36 047 and EP 0 072 462 describe, besides other topical dosage forms, gels comprising various arylacetic acid and arylpropionic acid derivatives of which only flurbiprofen, also in the form of a preparation containing 1%, was tested for antiinflammatory activity in animals. These gels also contain further auxiliary materials as solubilizers in addition to the carboxyvinyl polymer.

Although in some of the above-mentioned publications for the preparations of the gels various gel-forming agents have been enumerated, in the examples only carboxyvinyl polymers containing acidic groups (Carbopol ® and Hiviswako ®) were used as gelling agents. However, since the gel formation occurs only in a neutral or alkaline medium, not only the carboxyvinyl polymer but also the acidic active substance had to be neutralized. For the neutralization water-soluble organic amines are preferred, and, in some cases are alkali bases. This necessarily results in a formation of salts of the active substances.

However, a locally applicable medicament will function efficiently and rapidly only if the active substrate penetrates through the skin. Therefore, the active substance preferably should be in the dissolved state. The above-mentioned formation of salts will be expected to improve the solubility of the active ingredients.

None of the prior art examples describe gels containing more than 3% of an arylpropionic derivative as the active ingredient. Even when additional solubilizers or surfactants of various kinds are employed, this concentration of active ingredient is not exceeded. It can be concluded therefrom that a conventional gel base containing carboxyvinyl polymer is not suitable for preparing gels containing a higher percentage of arylpropionic acid derivatives.

The arylpropionic acid derivatives, although they are soluble in some physiologically compatible vehicles, nevertheless will immediately precipitate upon addition of even a small amount of water. Thereby the arylpropionic acid derivatives, even if they remain dispersed in the water-containing gel composition, will be prevented from undergoing a rapid absorption through the skin.

From H.P. Fiedler, "Lexikon der Hilfsstoffe fur Pharmazie, Kosmetik und angrenzende Gebiete", Editio Cantor Aulendorf, 1981, page 720 and The Merck Index, 10th Edition, 1983, No. 7432, respectively, are known polyoxyethylene-polyoxpropylene copolymers (Pluronicc ® and Poloxamer ®, respectively) as carrier materials some types of which are also capable of forming gels under appropriate conditions.

From U.S. Pat. No. 4,511,563 it is known to prepare clear analgesic gels having reduced tackiness from neutral or baseneutralizied analgesics such as triethanolamine salicylate, camphor, phenolcamphor, menthol, etc. by processing from 10 to 40 parts of non-ionic wetting agents such as polyoxyethylenepolyoxypropylene copolymers with water and 5 to 40 parts of glycerol into gels. Glycerol is an important component of the gels, as it reduces the tackiness and promotes the gel formation.

It was the object of the present invention to develop transdermally absorbable water-containing preparations of arylpropionic acid derivatives which preferably are in the form of gels and to assure at least a sufficient absorption with good compatibility, without requirement of neutralization with bases.

Surprisingly, it has been found that a significantly improved and accelerated absorption of the active substances can be achieved, if the preparations contain, in addition to 1 to 15% by weight of the active ingredient, from 10 to 40% by weight of polyoxyethylene polyoxypropylene copolymers, from 10 to 50% by weight of one or more physiologically acceptable organic solvents, optionally up to 1% by weight of preservatives, colorants and/or perfumes, and at least 10% by weight of water.

Suitable polyoxyethylene polyoxypropylene copolymers have relative molecular weights of from 1,000 to 13,000. If the relative molecular weight is in excess of 6,000, it is possible to also prepare the preparations according to the present invention such as to form gels. Besides 1 to 10% by weight of the active ingredient, from 15 to 32% by weight of polyoxyethylene polyoxypropylene copolymers, from 17 to 44% by weight of one or more physiologically acceptable organic solvents, optionally up to 1% by weight of preservatives, colorants and/or perfumes, are used. The water content of these gels is usually more than 30%.

The polyoxyethylene-polyoxypropylene copolymers are commercially available and, for example, are offered under the designations of Pluronic ® and Poloxamer ®. They are physiologically compatible and, thus, suitable as auxiliary materials for the preparation of transdermally applicable medicaments.

As the physiologically compatible organic solvents there can be used, for example, dimethyl sulfoxide or mono-, di-, or trihydroxy straight-chain, branched or cyclic alcohols having from 2 to 6 carbon atoms in the carbon backbone, into which also up to 2 oxygen atoms may have been inserted, or polyoxyalcohol fatty alcohol ethers or mixtures thereof. Ethanol, isopropanol, 1,2-propane diol, glycerol, isosorbide, dimethylisosorbide, polyoxyethylene-(4)-lauryl ether, polyoxypropylene-(15)-stearyl ether as well as dimethyl sulfoxide have proven to be useful.

The process for producing the transdermally absorbable water-containing preparations of arylpropionic acid derivatives of the present invention is carried out by heating the stirred components, optionally under elevated pressure, at from 40° C. to 90° C. and then coolng them again. The elevated pressure is especially required where the employed organic solvents would otherwise evaporate under the reaction conditions. An excess pressure of from 0.2 to 1 bar is sufficient; it is preferred to operate within the range of from 0.2 to 0.5 bar.

For preparation of gels, it is required to select the relative molecular weight of the polyoxyethylene-polyoxypropylene copolymers so that it is at least 6,000. Products having relative molecular weights of more than 13,000 appear to not be commercially available so far.

In the preparation of gels, it is further observed that the ratios of active ingredient, copolymer and organic solvent are chosen so as to result in ranges of from 1 to 10% by weight of the active ingredient, from 15 to 32% by weight of polyoxyethylene polyoxypropylene copolymers and from 17 to 44% by weight of the organic solvent. If a composition falling in this range does not solidify to form a gel, the intended objective can be reached by a simple variation of the ratio of ingredients.

The dissolution of the active ingredients in the mixture is preferably effected by stirring. Cooling the mixture to room temperature may also be accompanied by stirring.

Typical preparations according to the present invention and especially preparations obtained in the form of gels, are illustrated in detail hereinbelow.

EXAMPLE 1

20.0 kg of ibuprofen
64.0 kg of isopropanol
40.0 kg of dimethylisosorbide
64.0 kg of polyoxyethylene-polyoxypropylene copolymer 12500 (Pluronic ® F 127, Wyandotte Chemicals Corp.)
211.7 kg of water are thoroughly mixed for 10 minutes. The mixture is then heated at 85° C. with stirring and under slightly elevated pressure (by 0.3 bar) and maintained at this temperature for 15 minutes. Then it is allowed to cool to 65° C. and admixed with aroma materials (0.1 kg of lavender oil and 0.2 kg of neroli oil). The solution is cooled to room temperature with stirring. During the cooling phase the solution begins to gel at a temperature of about 45° C. to form a clear gel. The gel contains 5% of ibuprofen.

EXAMPLE 2

7.500 g of ibuprofen
15.925 g of isopropanol
10.000 g of dimethylisosorbide
16.000 g of polyoxyethylene-polyoxypropylene copolymer 12500 (Pluronic ® F 127, Wyandotte Chemicals Corp.)
50.500 g of water
0.025 g of lavender oil
0.050 g of neroli oil are processed as described in Example 1. The gel contains 7.5% of ibuprofen.

EXAMPLE 3

10.000 g of ibuprofen
15.925 g of isopropanol
12.000 g of dimethylisosorbide
18.000 g of polyoxyethylene-polyoxypropylene copolymer 12500 (Pluronic ® F 127, Wyandotte Chemicals Corp.)
44.000 g of water
0.025 g of lavender oil
0.050 g of neroli oil are processed as described in Example 1. The gel contains 10% of ibuprofen.

EXAMPLE 4

5.00 g of ibuprofen
16.00 g of isopropanol
10.00 g of glycerol
16.00 g of polyoxyethylene-polyoxypropylene copolymer 12500 (Pluronic ® F 127, Wyandotte Chemicals Corp.)
53.00 g of water are thoroughly mixed for 10 minutes. The mixture is then heated at 85° C. with stirring and under slightly elevated pressure (by 0.3 bar) and maintained at this temperature for 15 minutes. The solution is cooled to room temperature with stirring. During the cooling phase the solution begins to gel at a temperature of about 45° C. to form a clear gel. The gel contains 5% of ibuprofen.

EXAMPLE 5

5.00 g of ibuprofen
16.00 g of isopropanol
10.00 g of dimethylsulfoxide
16.00 g of polyoxyethylene-polyoxypropylene copolymer 12500 (Pluronic® 127, Wyandotte Chemicals Corp.)
53.00 g of water are processed as described in Example 4. The gel contains 5% of ibuprofen.

EXAMPLE 6

5.00 g of ibuprofen
17.90 g of isopropanol
17.90 g of polyoxyethylene-polyoxypropylene copolymer 12500 (Pluronic® F 127. Wyandotte Chemicals Corp.)
59.20 g of water are processed as described in Example 4. The gel contains 5% of ibuprofen.

EXAMPLE 7

5.00 g of ibuprofen
31.00 g of dimethylisosorbide
15.50 g of polyoxyethylene-polyoxypropylene copolymer 12500 (Pluronic® F 127, Wyandotte Chemicals Corp.)
48.50 g of water are processed in Example 4. The gel contains 5% of ibuprofen.

EXAMPLE 8

5.00 g of ibuprofen
35.00 g of dimethylsulfoxide
15.50 g of polyoxyethylene-polyoxypropylene copolymer 12500 (Pluronic® F 127, Wyandotte Chemicals Corp.)
44.50 g of water are processed in Example 4. The gel contains 5% of ibuprofen.

EXAMPLE 9

5.00 g of ibuprofen
14.00 g of isopropanol
10.00 g of dimethylisosorbide
30.00 g of polyoxyethylene-polyoxypropylene copolymer 6500 (Pluronic® F 105, Wyandotte Chemicals Corp.)
41.00 g of water are processed in Example 4. The gel contains 5% of ibuprofen.

EXAMPLE 10

5.00 g of ibuprofen
18.46 g of ethanol
11.54 g of 1,2-propanediol
15.50 g of polyoxyethylene-polyoxypropylene copolymer 12500 (Pluronic® F 127, Wyandotte Chemicals Corp.)
49.50 g of water are processed as described in Example 4. The gel contains 5% of ibuprofen.

EXAMPLE 11

5.00 g of ibuprofen
10.00 g of ethanol
18.00 g of isosorbide
15.50 g of polyoxyethylene-polyoxypropylene copolymer 12500 (Pluronic® F 127, Wyandotte Chemicals Corp.)
51.50 g of water are processed as described in Example 4. The gel contains 5% of ibuprofen.

EXAMPLE 12

5.00 g of flurbiprofen
17.00 g of isopropanol
10.00 g of dimethylisosorbide
16.00 g of polyoxyethylene-polyoxypropylene copolymer 12500 (Pluronic® F 127, Wyandotte Chemicals Corp.)
52.00 g of water are processed as described in Example 4. The gel contains 5% of flurbiprofen.

EXAMPLE 13

4.00 g of ketoprofen
15.00 g of isopropanol
7.50 g of dimethylisosorbide
23.50 g of polyoxyethylene-polyoxypropylene copolymer 12500 (Pluronic® F 127, Wyandotte Chemicals Corp.)
50.00 g of water are processed as described in Example 4. The gel contains 4% of ketoprofen.

EXAMPLE 14

4.00 g of naproxen
12.00 g of isopropanol
30.00 g of dimethylsulfoxide
22.00 g of polyoxyethylene-polyoxypropylene copolymer 12500 (Pluronic® F 127, Wyandotte Chemicals Corp.)
32.00 g of water are processed as described in Example 4. The gel contains 4% of naproxen.

EXAMPLE 15

4.00 g of naproxen
10.00 g of ethanol
30.00 g of dimethylsulfoxide
24.00 g of polyoxyethylene-polyoxypropylene copolymer 12500 (Pluronic® F 127, Wyandotte Chemicals Corp.)
32.00 g of water are processed as described in Example 4. The gel contains 4% of naproxen.

EXAMPLE 16

5.00 g of ibuprofen
19.00 g of isopropanol
10.00 g of dimethylisosorbide
10.00 g of polyoxyethylene-polyoxypropylene copolymer 12500 (Pluronic® F 127, Wyandotte Chemicals Corp.)
56.00 g of water are stirred and heated at 50° C., and stirring is continued until a clear solution has been formed. Then the composition is cooled to room temperature while the stirrer is operating. The lotion contains 5% of ibuprofen.

EXAMPLE 17

15.00 g of ibuprofen 35.00 g of isopropanol
15.00 g of dimethylisosorbide
25.00 g of polyoxyethylene-polyoxypropylene copolymer 1900 (Pluronic ® L 35, Wyandotte Chemicals Corp.)
10.00 g of water
are processed at 40° C. as described in Example 16. The lotion contains 15% of ibuprofen.

EXAMPLE 18

15.00 g of ibuprofen
30.00 g of isopropanol
15.00 g of dimethylisosorbide
25.00 g of polyoxyethylene-polyoxypropylene copolymer 1900 (Pluronic ® L 35, Wyandotte Chemicals Corp.)
15.00 g of water
are processed at 40° C. as described in Example 16. The lotion contains 15% of ibuprofen.

EXAMPLE 19

5.00 g of ketoprofen
17.00 g of isopropanol
10.00 g of dimethylisosorbide
16.00 g of polyoxyethylene-polyoxypropylene copolymer 12500 (Pluronic ® F 127, Wyandotte Chemicals Corp.)
52.00 g of water
are processed as described in Example 16. The lotion contains 5% of ketoprofen.

EXAMPLE 20

4.00 g of naproxen
17.00 g of isopropanol
15.00 g of dimethylisosorbide
30.00 g of polyoxyethylene-polyoxypropylene copolymer 12500 (Pluronic ® F 127, Wyandotte Chemicals Corp.)
34.00 g of water
are processed as described in Example 16. The Lotion contains 4% of naproxen.

EXAMPLE 21

10.000 g of ibuprofen
18.000 g of isopropanol
10.000 g of dimethylisosorbide
2.000 g of polyoxypropylene-(15)-stearylether
19.000 g of polyoxyethylene-polyoxypropylene copolymer 12500 (Pluronic ® F 127, Wyandotte Chemicals Corp.)
40.925 g of water
0.025 g of lavender oil
0.050 g of neroli oil
are processed as described in Example 1. The gel contains 10% of ibuprofen.

EXAMPLE 22

5.00 g of ibuprofen
16.00 g of isopropanol
10.00 g of dimethylisosorbide
1.00 g of polyoxyethylene-(4)-laurylether
16.00 g of polyoxyethylene-polyoxypropylene copolymer 12500 (Pluronic ® 127, Wyandotte Chemicals Corp.)
52.00 g of water
are processed as described in Example 4. The gel contains 5% of ibuprofen.

EXAMPLE 23

0.400 kg of ibuprofen
1.200 kg of isopropanol
0.800 kg of dimethylisosorbide
1.280 kg of polyoxyethylene-polyoxypropylene copolymer 12500 (Pluronic ® F 127, Wyandotte Chemicals Corp.)
4.234 kg of water
are thoroughly mixed for 10 minutes. The mixture is then heated at 85° C. with stirring and under slightly elevated pressure (0.3 bar) and maintained at this temperature for 15 minutes. Then it is allowed to cool to 65° C. and admixed with benzyl nicotinate (0.080 kg) and aroma materials (2 g of lavender oil and 4 g of neroli oil). The solution is cooled to room temperature with stirring. During the cooling phase the solution begins to gel at a temperature of about 45° C. to form a clear gel. The gel contains 5% of ibuprofen.

EXAMPLE 24

5.00 g of ibuprofen
16.00 g of isopropanol
10.00 g of dimethylisosorbide
16.00 g of polyoxyethylene-polyoxypropylene-copolymer 12500 (Pluronic ® F 127, Wyandotte Chemicals Corp.)
52.00 g of water
are thoroughly mixed for 10 minutes. The mixture is then heated at 85° C. with stirring and under slightly elevated pressure (0.3 bar) and maintained at this temperature for 15 minutes. Then it is allowed to cool to 65° C. and admixed with methyl salicylate and further treated as described in Example 23. The gel contains 5% of ibuprofen.

EXAMPLE 25

75.000 g ibuprofen
195.000 g isopropanol
253.875 g 2,2,-dimethyl-4-hydroxymethyl-1,3-dioxolane
217.500 g polyoxyethylene-polyoxypropylene-copolymer 12500 (Pluronic ® F 127, Wyandotte Chemicals Corp.)
757.500 g water
are intensively mixed for 10 minutes. The mixture is then heated with stirring under light pressure (0.3 bar) to 85° C. and left at that temperature for 15 minutes. The mixture is then cooled to 65° C. and treated with aromatic substances (0.375 g lavender oil and 0.750 g neroli oil). The solution is cooled to room temperature with constant mechanical stirring. During the cooling phase, the solution then starts to gel and at a temperature of about 45° C. forms a clear gel. The gel contains 5% ibuprofen.

EXAMPLE 26

5.000 g ibuprofen
15.925 g isopropanol
10.000 g α-tetrahydrofurfuryl-107 -hydroxypoly(oxyethylene)
16.000 g polyoxyethylene-polyoxypropylene copolymer 12500 (Pluronic ® F 127, Wyandotte Chemicals Corp.)
53.000 g water
mixed intensively for 10 minutes. The mixture is then heated to 85° C. with stirring under light pressure (0.3 bar) and left at that temperature for 15 minutes. Then, it is cooled to 65° C. and treated with aromatic substances (0.025 g lavender oil and 0.050 g neroli oil). The solution is cooled with constant stirring to room temperature.

During the cooling phase, the solution gels at a temperature of about 45° C. to a clear gel. The gel contains 5% ibuprofen.

The preparations according to the invention are applied depending on the type of disease to be treated. Preferably, the inflamed or painful region is anointed 3 to 6 times per day with a strand of gel 5 to 10 cm in length or the corresponding amount of liquid liniment so that 100 to 500 mg of arylpropionic acid derivative are administered. As indications there are considered degenerative and inflammatory articular diseases, soft tissue rheumatism, lumbago, myogeloses and traumatic states following sport injuries and accidents.

The bioavailability of a gel according to the present invention (Example 1) was investigated in comparison to a commercially available cream according to German Pat. No. DE-PS 32 05 504 and a gel according to European Application EP-OS 0 127 840 (Example 4) in eight test persons. On the upper part of the back of the test persons a skin area 20 cm x 20 cm in size was color-marked. On this area an amount of the test preparations corresponding to 300 mg of ibuprofen was applied. The preparations were anointed by an assistant whose hand was protected by a rubber glove. Prior to anointing and 0.25, 0.5, 1, 2, 4 and 6 hours after the application blood samples were taken. From the blood the plasma was recovered by centrifuging after addition of ethylenediaminetetraacetic acid, wherein the ibuprofen was determined by a HPLC separation using an electrochemical detector. The average values of the analytical results are shown as a curve in FIG. 1.

The bioavailability of a drug substance from a preparation is understood to mean the velocity and extent with which said drug substance is passed into the circulating blood. (E. Mutschler, Arzneimittel-Wirkungen, Wissenschaftl. Verlagsgesellschaft mbH, Stuttgart 1981).

According to F.H. Dost (Grundlagen der Pharmakokinetik, Georg Thieme Verlag, Stuttgart 1968) the area included by the blood level curve and the time axis (AUC=area under the curve) conforms to the amount of substance in the organism. This permits the comparison of the bioavailability of one substance from various application forms. From the course of the plasma levels as shown in FIG. 1 the AUC values were calculated, and the relative bioavailability of ibuprofen was determined (Table 1).

TABLE 1

|  | AUC values h × ng/ml | relative bioavailability | |
|---|---|---|---|
|  |  | EP-DS0127840 | DE-PS32055 |
| Gel according to Example 1 | 4388.8 | 2.45 | 1.38 |
| Commercially available cream according to DE-PS 32 05 504 | 3190.0 | 1.78 | 1 |
| Gel according to EP-OS 0 127 840 (Example 4) | 1788.2 | 1 | 0.56 |

From Table 1 it is apparent that with the gel preparation according to the present invention on the bioavailability of the active ingredient over a previously described gel preparation and a commercially available cream, respectively, has been improved by 145% and 38%, respectively.

Moreover, as is apparent from the comparison of the slopes of the plasma level curves of the two gel preparations, with the gel of the invention a more rapid supply of the active substance takes place than with the previously known gel. Thus, due to the more rapid release and higher bioavailability of the arylpropionic acid derivatives from the gel preparations according to the invention, better and more rapidly effective transdermally applicable medicaments are available than heretofore.

What is claimed is:

1. A transdermally absorbable water-containing analgesic, antirheumatic, antiinflammatory, gel preparation comprising from 5 to 10% of ibuprofen, from 10 to 40% by weight of polyoxyethylene polyoxypropylene copolymers, from 10 to 50% by weight of one or more physiologically acceptable organic solvents, optionally up to 1% by weight of preservatives, colorants and/or perfumes, and at least 10% by weight of water, said gel being free of neutralizing bases.

2. A preparation according to claim 1, which comprises from 15 to 32% by weight of polyoxyethylene polyoxypropylene copolymers, and from 17 to 44% by weight of one or more physiologically acceptable organic solvents.

3. A preparation according to claim 1, wherein the polyoxyethylene polyoxypropylene copolymers have relative molecular weights of from 1,000 to 13,000.

4. A preparation according to claim 1, characterized in that the polyoxyethylene polyoxypropylene copolymers have relative molecular weights of from 6,000 to 13,000.

5. A preparation according to claim 1, characterized in that as the physiologically acceptable organic solvents there are used dimethyl sulfoxide or mono-, di- or tri-hydroxy straight-chain, branched or cyclic alcohols having from 2 to 6 carbon atoms in the carbon backbone into which 0 to 2 oxygen atoms have been inserted, or polyoxyalkylene fatty alcohol ethers or mixtures thereof.

6. A preparation according to claim 5, characterized in that there are used as solvents ethanol, isopropanol, 1,2-propanediol, glycerol, isosorbide, dimethylisosorbide, polyoxyethylene-(4)-lauryl ether, polyoxypropylene-(15)-stearyl ether or mixtures thereof.

7. A preparation according to claim 1, characterized in that it further comprises up to 2% by weight of a blood circulation-promoting or rubefacient substance selected from the group consisting of benzyl nicotinate and a salicylate.

8. A preparation according to claim 7, characterized in that the blood circulation-promoting or rubefacient substance is benzyl nicotinate.

9. A preparation according to claim 7, characterized in that the blood circulation-promoting or rubefacient substance is a salicylate.

10. A process for making a transdermally absorbable water-containing antirheumatic, anti-inflammatory, analgesic gel characterized in that a mixture comprising from 5 to 10% by weight of ibuprofen as an active ingredient, from 10 to 40% by weight of polyoxyethylene polyoxypropylene copolymers, from 10 to 50% by weight of one or more physiologically acceptable organic solvents, optionally up to 1% by weight of preservatives, colorants and/or perfumes, and at least 10% by weight of water are heated with stirring at from 40° C. to 90° C. in the absence of neutralizing bases then cooled.

11. The process for making a gel according to claim 10, characterized in that from 15 to 32% by weight of polyoxyethylene polyoxypropylene copolymers and from 17 to 44% by weight of one or more physiologically acceptable organic solvents are heated at from 80° C. to 90° C. in the absence of neutralizing bases and then cooled.

12. The process according to claim 10, characterized in that, as the physiologically acceptable organic solvents there are used dimethyl sulfoxide or mono-, di- or trihydroxy straight-chain, branched or cyclic alcohols having from 2 to 6 carbon atoms and 0 to 2 oxygen atoms in the carbon backbone or polyoxyalkylene fatty alcohol ethers or mixtures thereof.

13. The process according to claim 12, characterized in that there are used as solvents ethanol, isopropanol, 1,2-propanediol, glycerol, isosorbide, dimethylisosorbide, polyoxyethylene-(4)-lauryl ether, polyoxypropylene-(15)-stearyl ether or mixtures thereof.

14. The process according to claim 10, characterized in that the mixture further comprises up to 2% by weight of a blood circulation-promoting or rubefacient substance selected from the group consisting of a benzyl nicotinate and a salicylate.

15. The process according to claim 14, characterized in that the blood circulation-promoting or rubefacient substance is benzyl nicotinate.

16. The process according to claim 14, characterized in that the blood circulation-promoting or rubefacient substance is a salicylate.

* * * * *